US006228096B1

(12) United States Patent
Marchand

(10) Patent No.: US 6,228,096 B1
(45) Date of Patent: May 8, 2001

(54) INSTRUMENT AND METHOD FOR MANIPULATING AN OPERATING MEMBER COUPLED TO SUTURE MATERIAL WHILE MAINTAINING TENSION ON THE SUTURE MATERIAL

(76) Inventor: Sam R. Marchand, 1170 Robmar, Dunedin, FL (US) 33528

( * ) Notice: Subject to any disclaimer, the term of this patent is extended or adjusted under 35 U.S.C. 154(b) by 0 days.

(21) Appl. No.: 09/281,938

(22) Filed: Mar. 31, 1999

(51) Int. Cl.[7] .............................. A61B 17/10; A61B 17/04
(52) U.S. Cl. ............................................ 606/139; 606/232
(58) Field of Search ........................... 606/139, 144–148, 606/140–143

(56) References Cited

U.S. PATENT DOCUMENTS

| 3,687,138 | * | 8/1972 | Jarvik ................................. 128/322 |
| 4,890,615 | * | 1/1990 | Caspari et al. ...................... 606/146 |
| 4,898,156 | | 2/1990 | Gatturna et al. . |
| 5,041,129 | | 8/1991 | Hayhurst et al. . |
| 5,203,787 | | 4/1993 | Noblitt et al. . |
| 5,250,055 | | 10/1993 | Moore et al. . |
| 5,403,348 | | 4/1995 | Bonutti . |
| 5,527,343 | | 6/1996 | Bonutti . |
| 5,531,762 | | 7/1996 | Stone et al. . |
| 5,534,011 | | 7/1996 | Greene, Jr. et al. . |
| 5,569,303 | | 10/1996 | Johnson . |
| 5,569,305 | | 10/1996 | Bonutti . |
| 5,569,306 | | 10/1996 | Thal . |
| 5,601,557 | | 2/1997 | Hayhurst . |
| 5,601,558 | | 2/1997 | Torrie et al. . |
| 5,713,910 | * | 2/1998 | Gordon et al. ...................... 606/144 |
| 5,741,279 | * | 4/1998 | Gordon et al. ...................... 606/144 |
| 5,746,752 | * | 5/1998 | Burkhart ............................. 606/139 |
| 5,810,848 | * | 9/1998 | Hayhurst ............................ 606/144 |
| 5,960,992 | * | 1/1999 | Daniel et al. ....................... 606/145 |

\* cited by examiner

Primary Examiner—Gary Jackson
Assistant Examiner—(Jackie) Tan-Uyen T. Ho

(57) ABSTRACT

An instrument and method for manipulating an operating member during a surgical procedure. The operating member has suture attached thereto and is supported at a distal end of the instrument. Tension is maintained on the suture material while the operating member is manipulated. For example, the operating member can be a suture anchor that is inserted through a hole formed in hard tissue and oriented to span the hole while tension is maintained on the suture material.

4 Claims, 11 Drawing Sheets

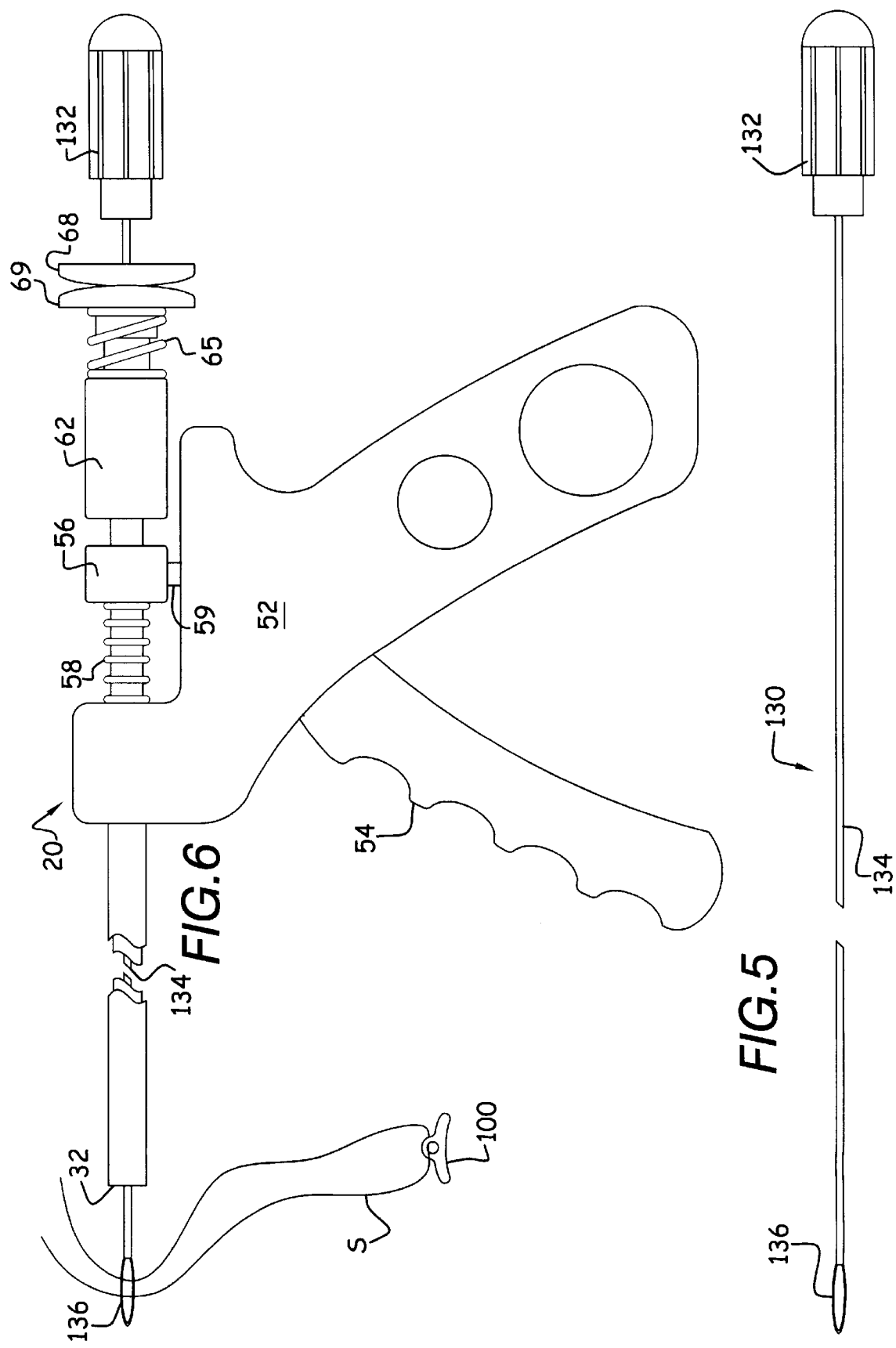

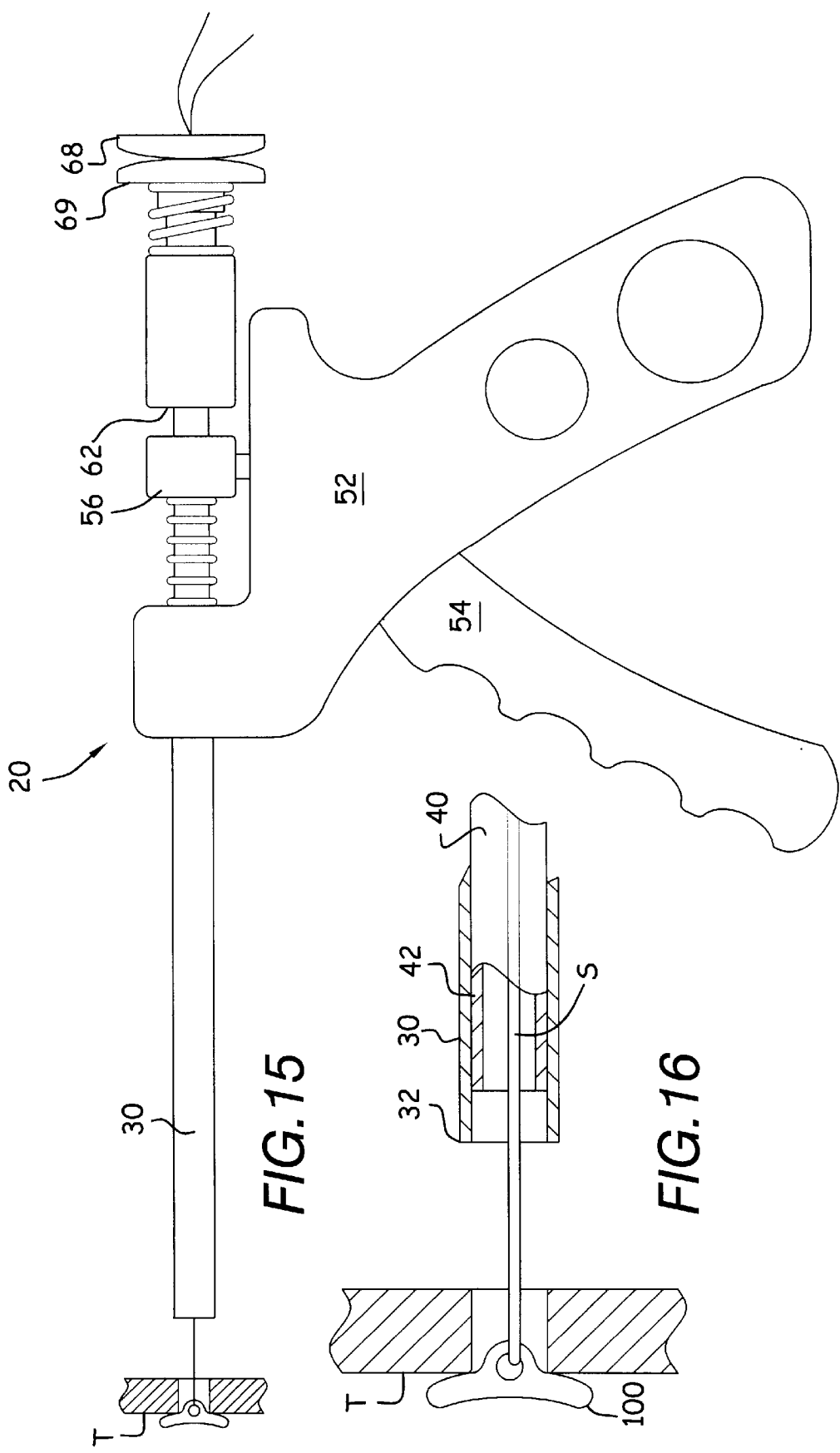

INSTRUMENT AND METHOD FOR MANIPULATING AN OPERATING MEMBER COUPLED TO SUTURE MATERIAL WHILE MAINTAINING TENSION ON THE SUTURE MATERIAL

BACKGROUND OF THE INVENTION

1. Field of the Invention

The invention relates to an instrument and method for manipulating an operating member that is attached to suture material while maintaining tension on the suture material.

2. Description of the Related Art

In many anatomical structures, soft tissue, such as tendons and ligaments, are inserted into bone tissue through small collagenous fibers. Such structures are very strong thus permitting muscles to affect force on the bone through the tendons or permitting the ligaments to stabilize the bone. Notwithstanding the strength of such structures, various injuries and degeneration often occur in which the soft tissue is torn away from the bone. Various procedures have been developed for reattaching soft tissue to bone tissue.

For example, it is known to utilize screws, staples, cement, or suture material to attach soft tissue to bone tissue. It is also known to insert a suture anchor into a cavity formed in bone tissue. Typically, a suture anchor has sharp burrs, threads, or the like which engage with or bite into surfaces defining the cavity in the bone tissue, and a portion to which a length of suture material is attached. The other end of the suture material is coupled to soft tissue by suturing, tying, or another procedure before or after insertion of the suture anchor into the cavity. Accordingly, soft tissue or the like can be attached to bone tissue to repair damage. However, often density of bone tissue is very low thus rendering it difficult to securely fix an anchor in a bone cavity.

For example, it often is desirable to reattach tendons or other soft tissue to the humerus. However, in most people over the age of 30, the cancellous bone in the humerus has absorbed to the point where the density of the bone is very low and, in some cases, only the cortical bone remains. Of course, when bone density is very low, the strength of the bone tissue is also relatively low and thus it is difficult to reliably fix an anchor to the bone tissue by embedding the anchor in a cavity formed in the bone.

SUMMARY OF THE INVENTION

It is an object of the invention to conduct a surgical procedure with an operating member that is coupled to suture material while maintaining tension on the suture material.

It is another object of the invention to reliably attach soft tissue to bone tissue having low density.

It is another object of the invention to place a suture anchor across an opening formed in a bone while maintaining tension on suture attached to the suture anchor to permit the suture anchor to be pulled against the outer surface of the bone.

It is another object of the invention to insert a suture anchor having suture material coupled thereto through a hole formed in bone tissue in a first longitudinal orientation and subsequently turn the suture anchor, while maintaining tension on the suture material, to a transverse orientation to thereby bridge the hole.

It is another object of the invention to reliably insert a suture anchor in minimally invasive and open surgical procedures.

To achieve these objects, the invention is an instrument for conducting a procedure with an operating member that is coupled to suture material. The instrument includes a shaft, means for manipulating the operating member, a handle and a suture tension mechanism configured to grasp a free end of the suture material and retain tension on the suture material that is attached to the operating member when the operating member is received in the guide and pushed out of the distal end of the guide by the pusher.

In one aspect of the invention, the operating member is a suture anchor having a longitudinal axis and the instrument includes a tubular guide having a distal end and a proximal end that is configured to receive the suture anchor and a tubular pusher extending substantially through the guide and having a proximal end and a distal end that is configured to abut the suture anchor received in the distal end of the guide. A handle mechanism is coupled to the guide and the pusher and is operative to cause relative movement between the guide and the pusher to thereby push the suture anchor out of the distal end of the guide. The suture anchor is loaded in the guide with the longitudinal axis of the suture anchor extending substantially along the length of the guide, i.e. in a "longitudinal orientation", while inner surfaces of the guide retain the longitudinal orientation. While the suture is maintained under tension by the suture tension mechanism, the distal end of the guide can be placed adjacent or in a hole formed in bone tissue or other tissue and the handle mechanism can be operated to cause the pusher to move relative to the guide to thereby push the suture anchor out of the guide. When the suture anchor moves out of the confines of the guide and through the hole to the opposite side of the tissue, the tension on the suture material causes the suture anchor to assume a transverse orientation in which the longitudinal axis of the suture anchor is substantially transverse to the longitudinal axis of the guide. In the transverse orientation, the suture anchor bridges or spans the hole in the bone or other tissue to prevent the suture anchor from being pulled back through the hole. The suture tension mechanism can be disposed on the pusher to be movable with the pusher or otherwise configured to maintain a constant tension on the suture material regardless of the position of the pusher relative to the guide.

Another aspect of the invention is a method for manipulating an operating member during a surgical procedure while maintaining tension on suture material attached to the operating member.

BRIEF DESCRIPTION OF THE DRAWING

The invention will be described through a preferred embodiment illustrated in the drawing in which:

FIG. 5 is a side view of a threading tool for use with the instrument of FIG. 1;

FIG. 6 is a side view of the instrument of FIG. 1 with the tool of FIG. 5 inserted therethrough;

FIG. 15 is a side view of the instrument of FIG. 1 being withdrawn after inserting an anchor; and FIG. 16 is a sectional view of the distal end of the instrument in the position of FIG. 16.

DETAILED DESCRIPTION OF THE PREFERRED EMBODIMENT

Figure 1:
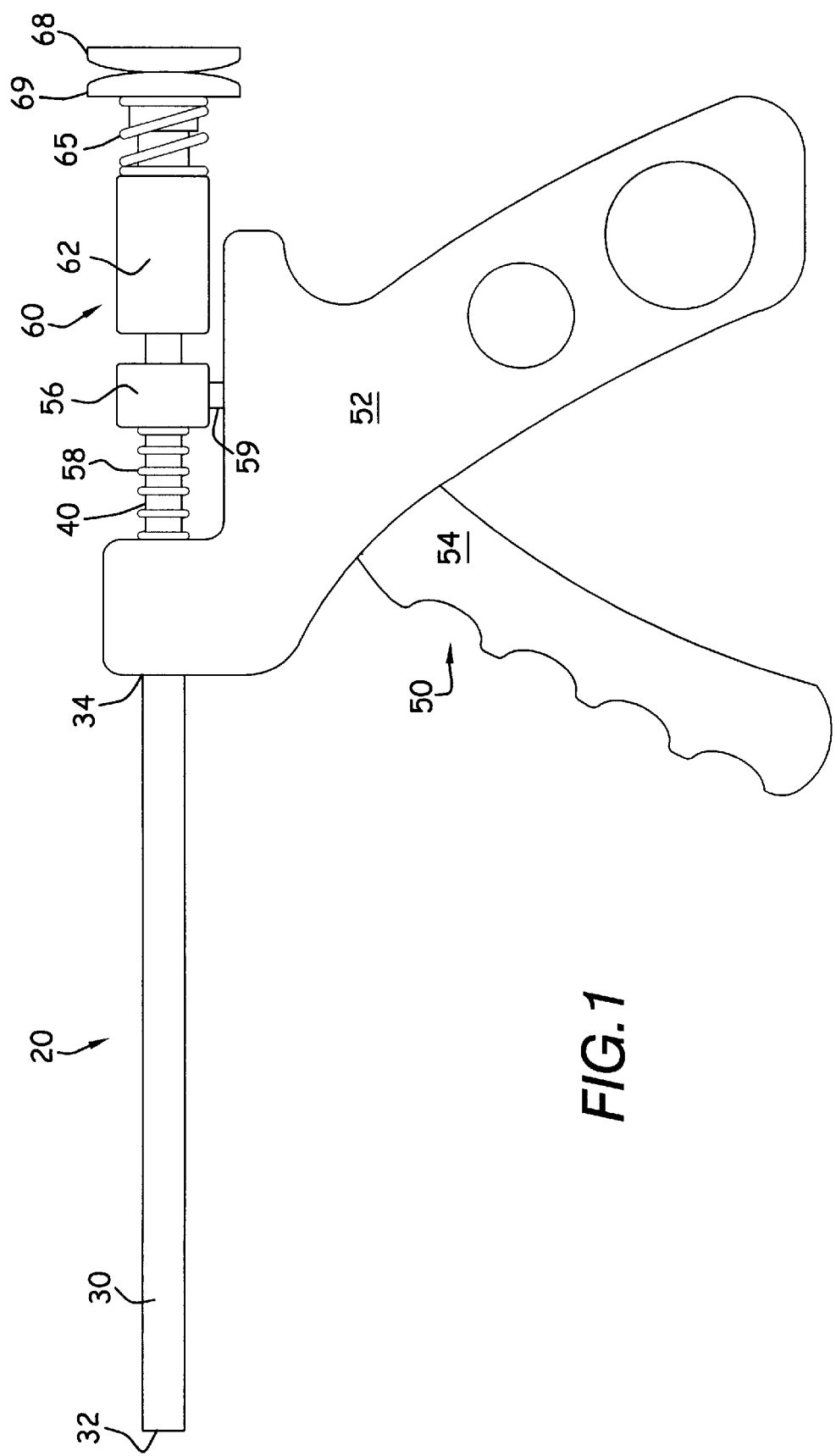
FIG. 1 is a side view of an instrument according to the invention.
Figure 2:
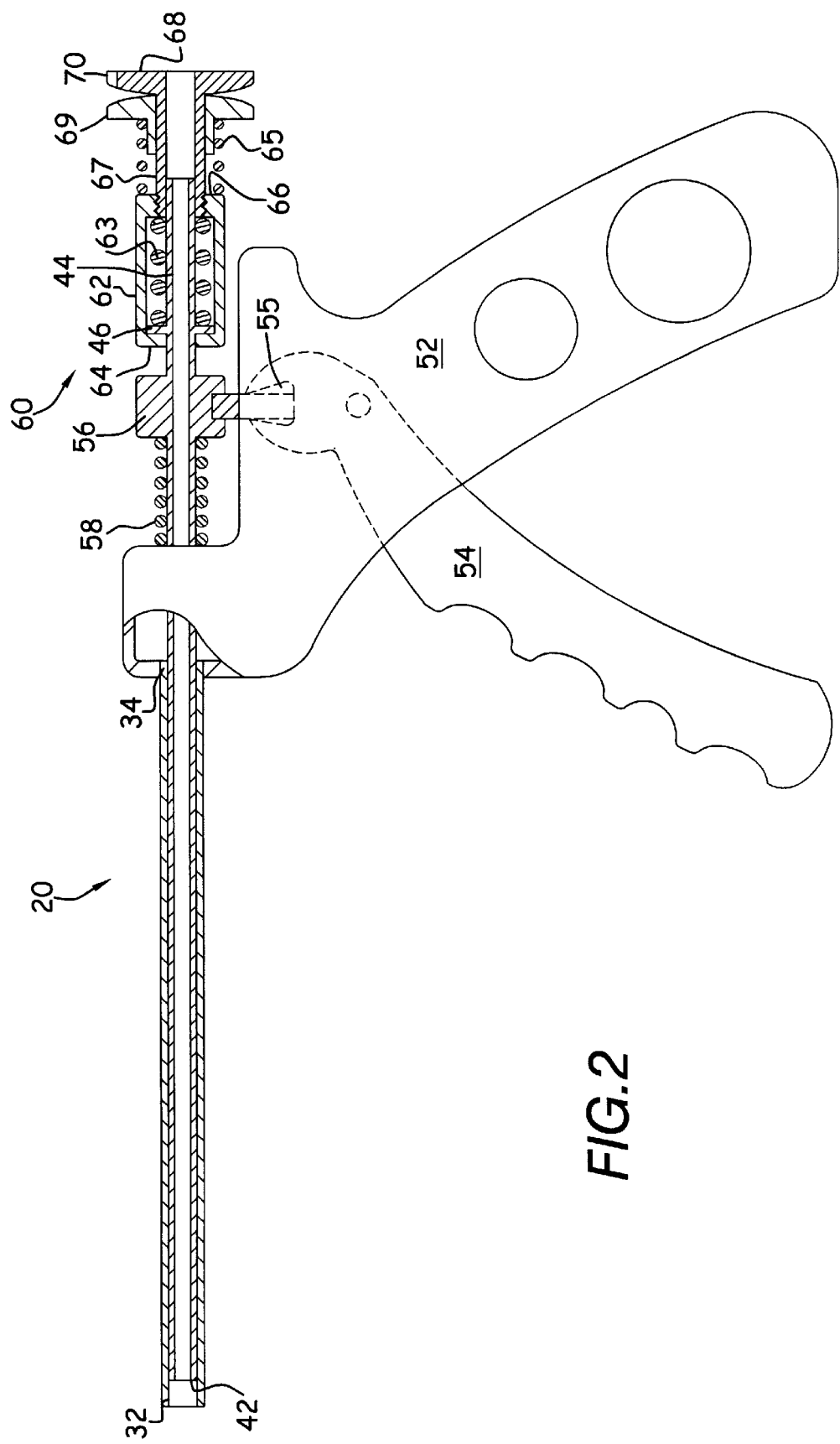
FIG. 2 is a side view of the instrument of FIG. 1 in partial section taken along line 2—2 of FIG. 3.
Figure 3:
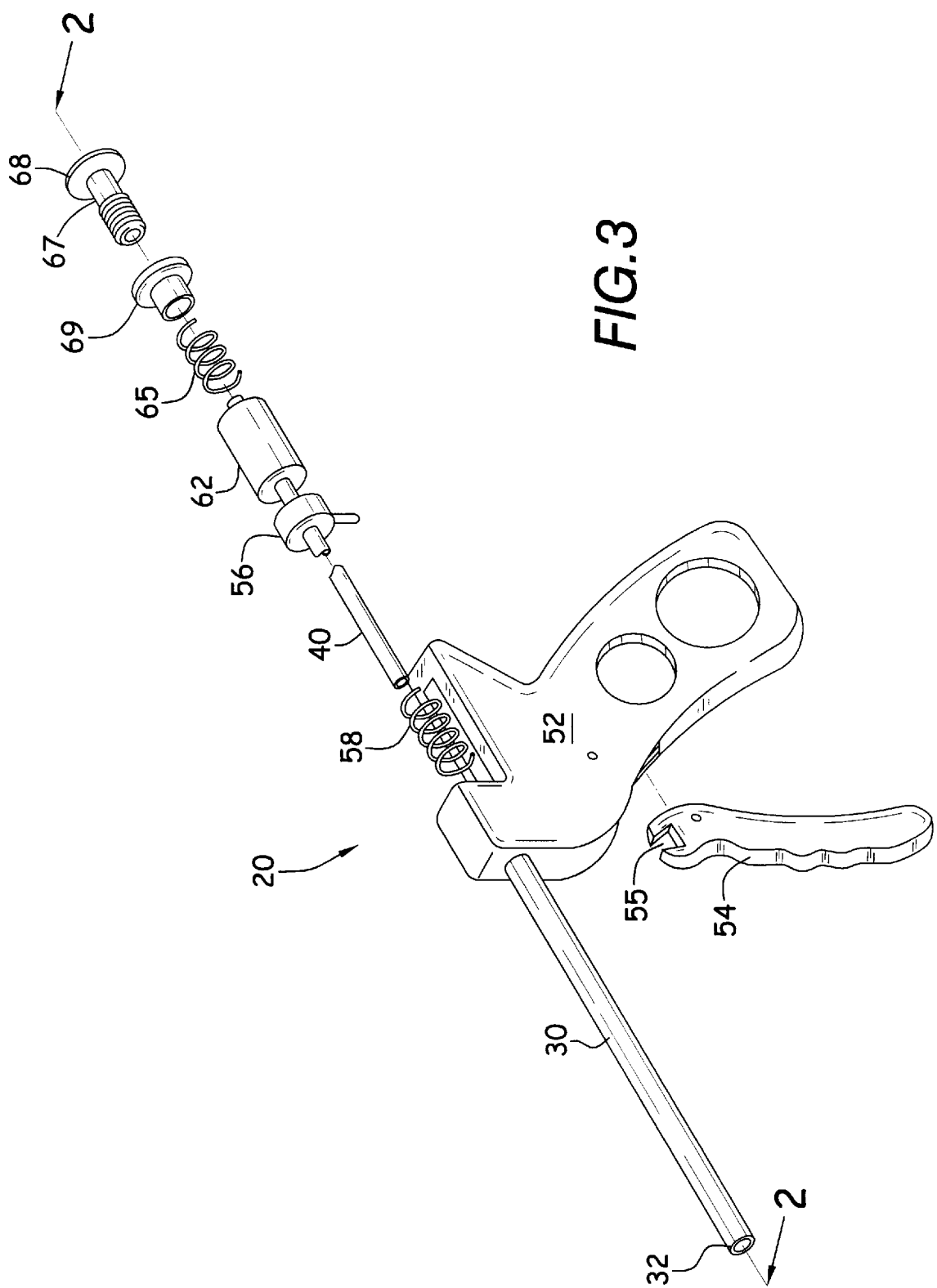
FIG. 3 is an exploded perspective view of the instrument of FIG. 1.

As illustrated in FIGS. 1–3, instrument 20 includes a shaft constituted of tubular guide 30 and tubular pusher or manipulating member 40, handle mechanism 50, and suture tension mechanism 60. Guide 30 and pusher 40 are in the form of elongated cylinders in the preferred embodiment. However, guide 30 and pusher 40 can be of any cross-sectional shape as long as pusher 40 can be inserted in guide 30 and a channel can be defined through or along instrument 20 for receiving suture material in the manner described below.

Guide 30 has distal end 32 that is configured to be loaded with an operating member and placed adjacent or into a hole formed through tissue in the manner described below. Guide 30 also has proximal end 34 that is coupled to fixed handle 52 of handle mechanism 50. Pusher 40 is slidingly disposed inside guide 30, has distal end 42 that extends substantially to distal end 32 of guide 30 (depending on the relative position of pusher 40 with respect to guide 30), and proximal end 44 that extends through fixed handle 52 beyond proximal end 34 of guide 30 (see FIG. 2). Distal end 42 and distal end 32 constitute means for manipulating the suture anchor in the preferred embodiment.

Figure 8:
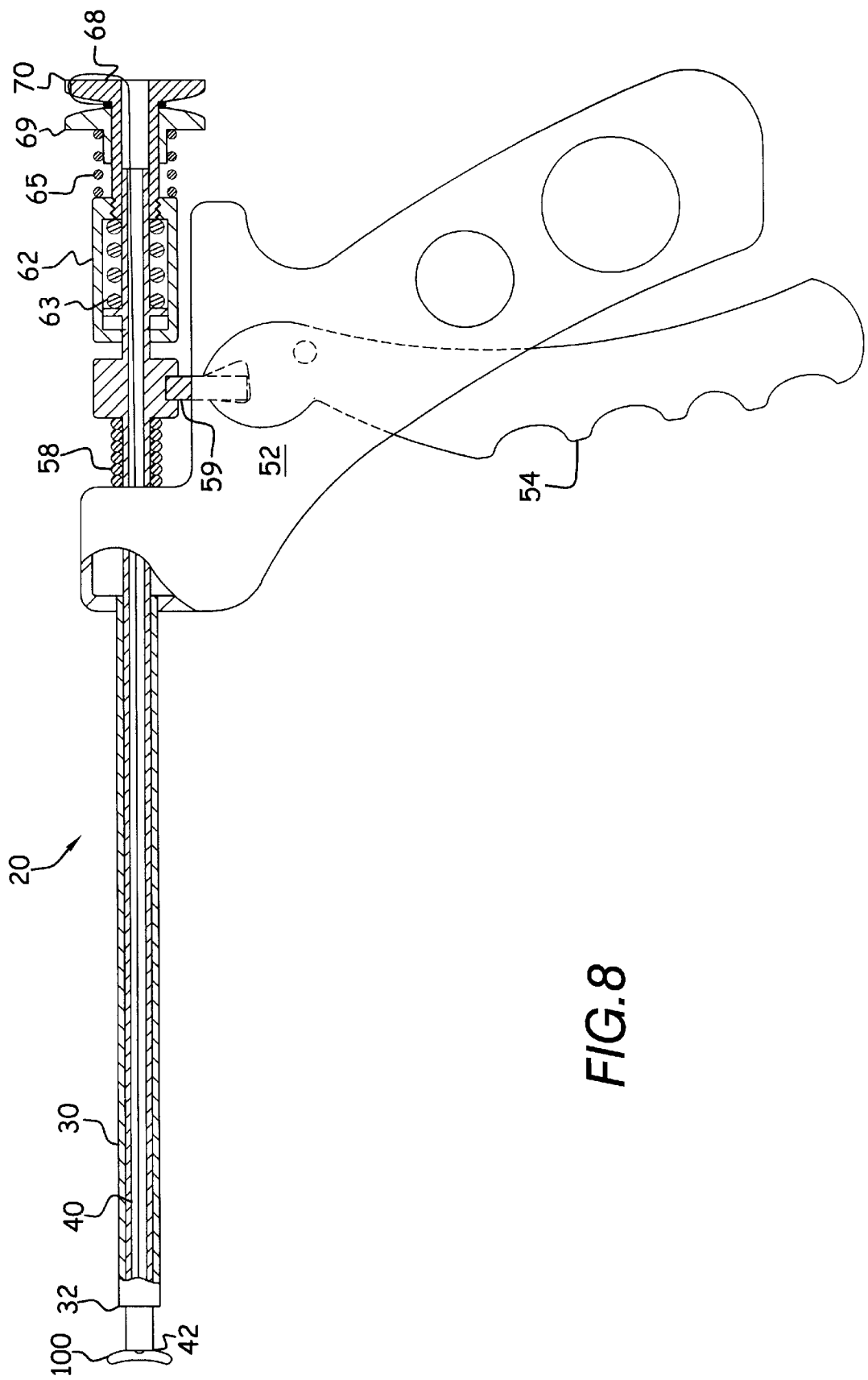
FIG. 8 is a side view, in partial section, of the instrument of FIG. 1 with the pusher extended for loading a suture.

Flange 56 having tab 59 extending therefrom is fixed on pusher 40 near proximal end 44. Pivotal handle 54 is pivotally mounted on fixed handle 52 and has notch 55 formed in a top portion thereof for receiving tab 59 as best illustrated in FIG. 2. When a lower portion of pivotal handle 54 is pressed towards fixed handle 52, the upper portion of pivotal handle 54 having notch 55 moves distally to cause pusher 40 to move distally with respect to guide 30, as illustrated in FIG. 8 for example. Fixed handle 52 and pivotal handle 54 are shaped to facilitate being grasped by one hand of the surgeon. Therefore, the surgeon need only tighten his grip to press a lower portion of pivotal handle 54 towards fixed handle 52. Coil spring 58 is disposed between an upper portion of fixed handle 52 and flange 56 to bias pusher 40 distally with respect to guide 30 and to thereby bias pivotal handle 54 away from fixed handle 52.

Suture tensioning mechanism 60 is disposed on pusher 40 near proximal end 44 and includes projection 46 in the form of an annular flange extending from pusher 40, barrel 62, having end faces 64 and 66 and respective openings formed in the end faces through which pusher 40 extends, slidingly disposed on guide 40 near proximal end 44, tube 67 extending from end face 66, flange 68 fixedly disposed on an end of tube 67, and flange 69 slidingly disposed on tube 67. Additionally, suture tensioning device 60 includes coil spring 63, serving as a biasing member, disposed between projection 46 and an inner surface of end face 66, and coil spring 65, also serving as a biasing member, disposed between an outer surface of end face 66 and flange 69. It can be seen that coil spring 63 biases barrel 62, flange 68, and flange 69 proximally with respect to pusher 40. Also, it can be seen that coil spring 65 biases flange 69 toward flange 68. The elements described above will be understood more clearly after the description of operation of instrument 20 set forth below.

Figure 4B:
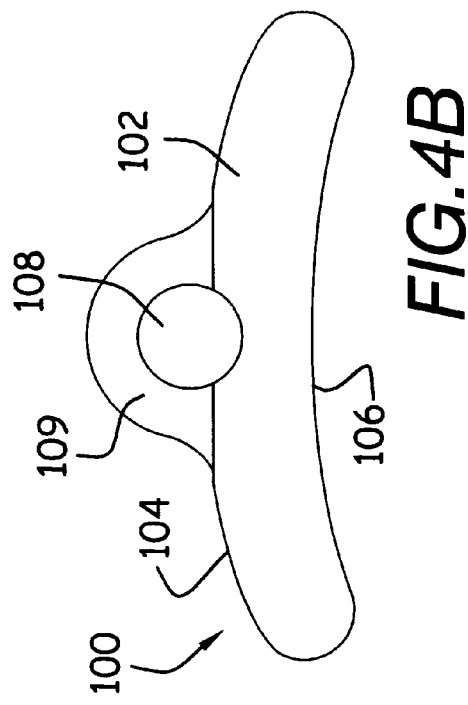
FIG. 4B is a side view of an anchor for use with the instrument.
Figure 4C:
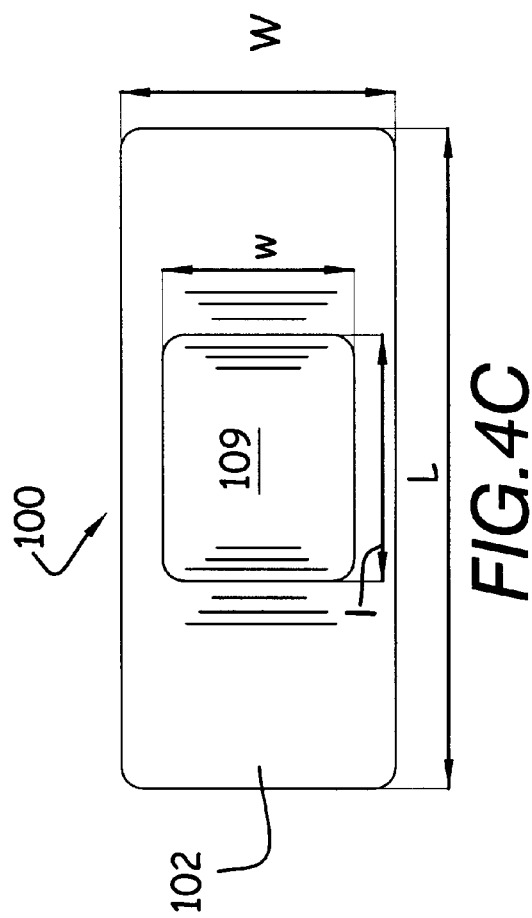
FIG. 4C is a top view of an anchor for use with the instrument.
Figure 4A:
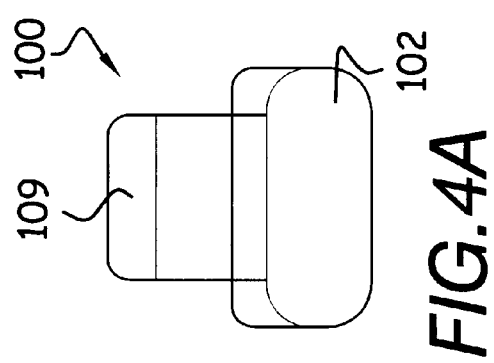
FIG. 4A is an end view of an anchor for use with the instrument.

Prior to an attachment procedure, suture anchor 100, as an operating member, is loaded into instrument 20. As illustrated in FIGS. 4A–4C, suture anchor 100 has arcuate body 102 having convex side 104 and concave side 106 (see FIG. 4B). Eyelet 108 is defined on a central portion of convex side 104 by a ring-like projection 109 or the like to permit attachment of suture material to suture anchor 100 as described below. Width w of ring-like projection 109 preferably is about half of width W of arcuate body 102, as illustrated in FIG. 4C. Also, length l of ring-like projection 109 preferably is about ⅓ of length L of arcuate body 102, also as illustrated in FIG. 4C.

FIG. 5 illustrates threading tool 130 for threading suture attached to anchor 100 through instrument 20 for loading suture anchor 100. Threading tool 130 includes elongated stem 134 having handle 132 at one end and loop 136 at another end. As illustrated in FIG. 6, stem 134 is inserted through pusher 40 and guide 30 from proximal end 44 until loop 136 extends from distal end 32. It is apparent that stem 134 should be long enough to extend through the entirety of instrument 20. With loop 136 extending out of distal end 32, end portions of suture material S are passed through loop 136, as illustrated in FIG. 6. Note that suture material S previously has been passed through eyelet 108 of suture anchor 100 with a central portion of suture material S being received in eyelet 108. With suture material S passed through loop 136, handle 132 is pulled in a proximal direction to withdraw stem 134 and loop 136 from instrument 20 to thereby pull the end portions of suture material S through pusher 40 and out of proximal end 44 as illustrated in FIG. 7.

Figure 7:
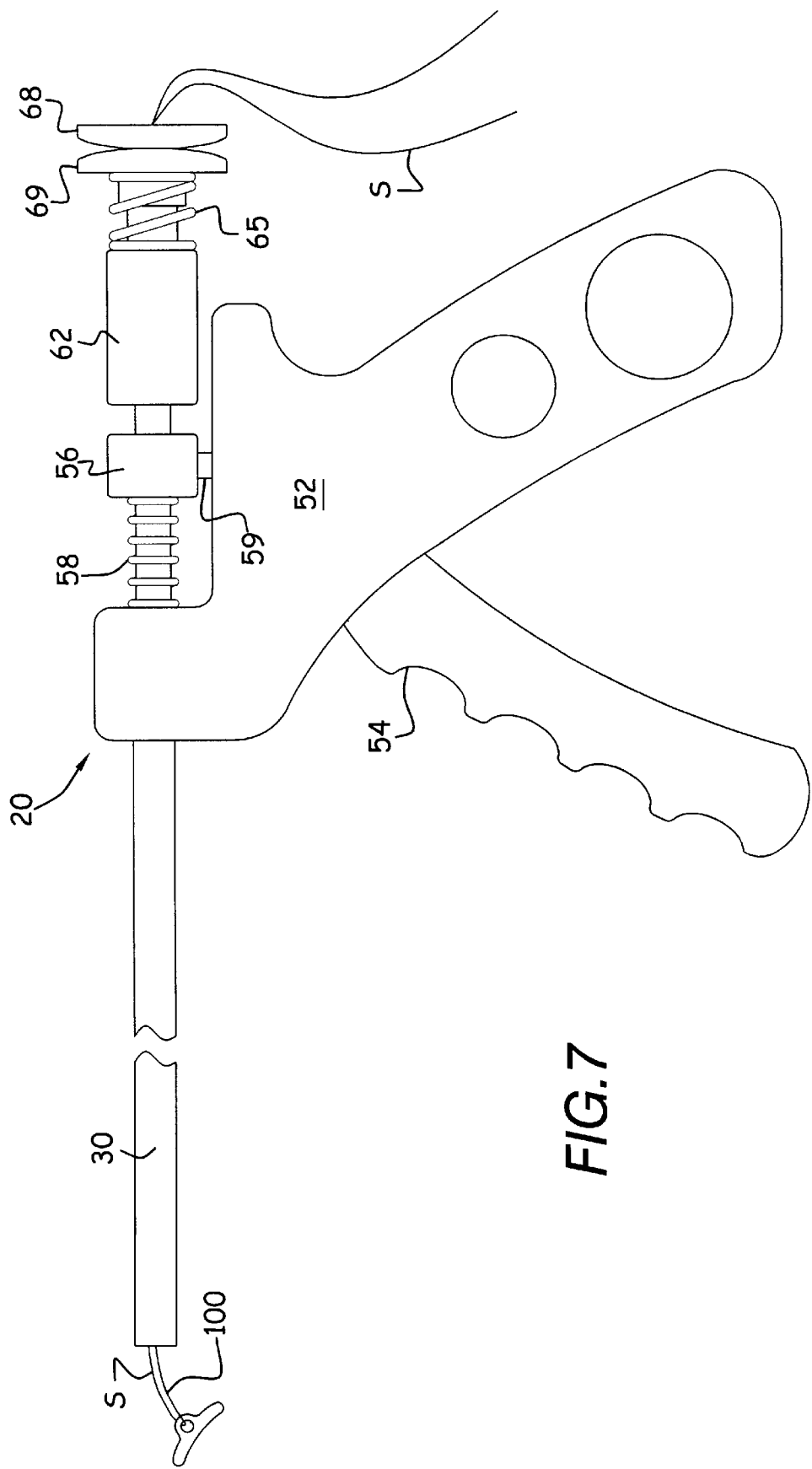
FIG. 7 is a side view of the instrument of FIG. 1 with suture material passed therethrough.

In the state illustrated in FIG. 7, a double length of suture material S extends through instrument 20, free ends of suture material S extend out of proximal end 44, and suture anchor 100 is coupled to a portion of suture material S that extends out of distal end 32. From the position illustrated in FIG. 7, pivotal handle 54 is compressed towards fixed handle 52 to cause distal end 42 of pusher 40 to extend beyond distal end 32 of guide 30 and the free ends of suture material S can be wrapped manually around tube 67 to thereby be gripped between flanges 68 and 69 as illustrated in FIG. 8. As suture material S is wrapped around tube 67, with tension in suture material S, suture material S is drawn between flanges 68 and 69 due to the tapered shape of the opposing faces of flanges 68 and 69. Spring 65 presses flange 69 towards flange 68 to secure suture material S. Also, slit 70 is provided in flange 68 to facilitate entry of suture material S between flanges 68 and 69 (see FIGS. 2 and 8). Ordinarily, two or three wraps of suture material S around tube 67 will be sufficient to secure the free ends of suture material S between flanges 68 and 69. It can be seen that tension can be applied to suture material S during the wrapping procedure to compress spring 63. Barrel 62 can be pushed distally while suture material S is wrapped around tube 67 to assist in placing suture material S under tension. Therefore, spring 63 will tend to push flanges 68 and 69 proximally while suture anchor 100 abuts distal end 42 and thus a constant tension will be maintained on suture material S.

Figures 9, 10:
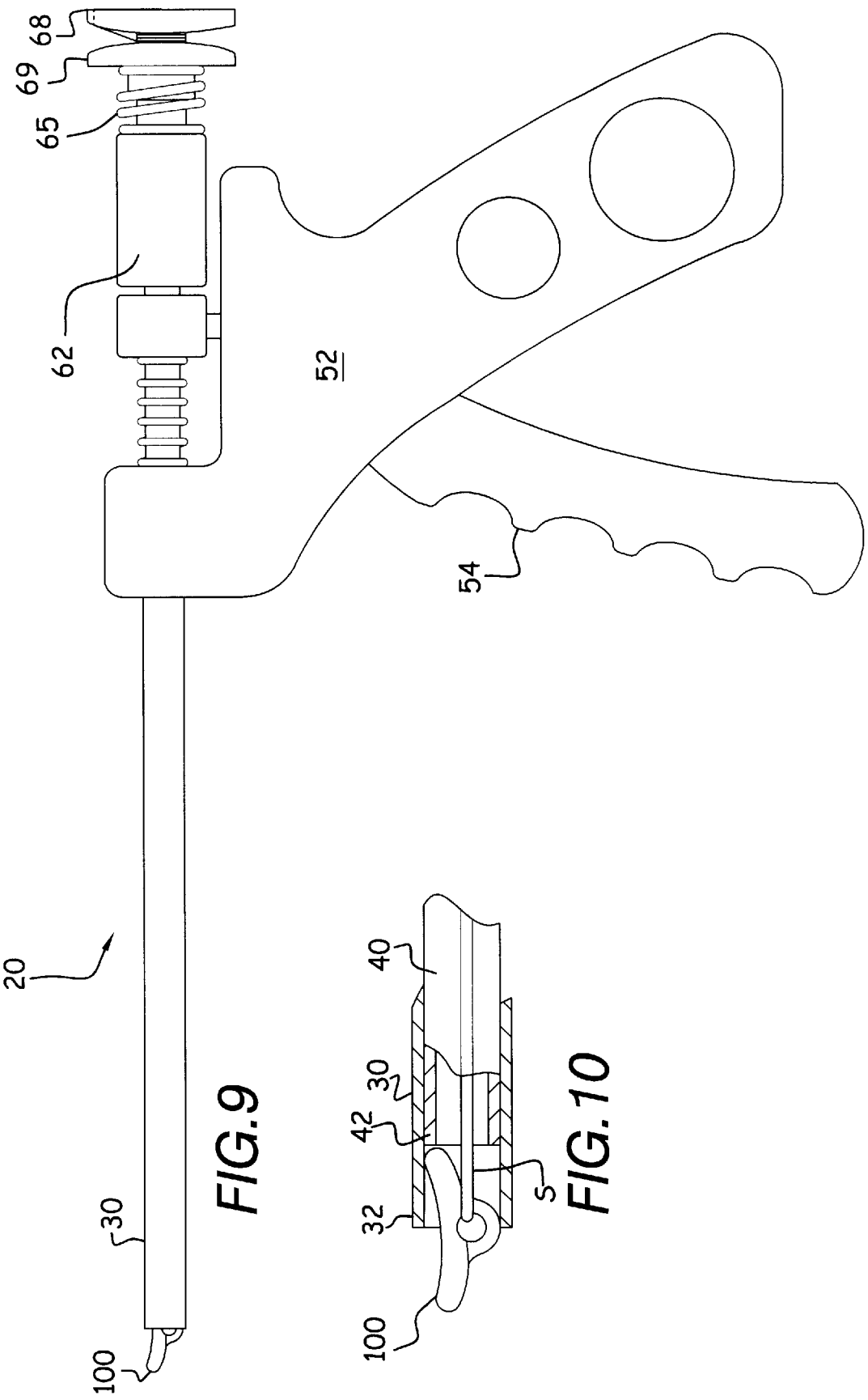
FIG. 9 is a side view of the instrument of FIG. 1 as an anchor is being drawn into the guide.
FIG. 10 is a sectional view of the distal end of the instrument in the position of FIG. 9.
Figure 11:
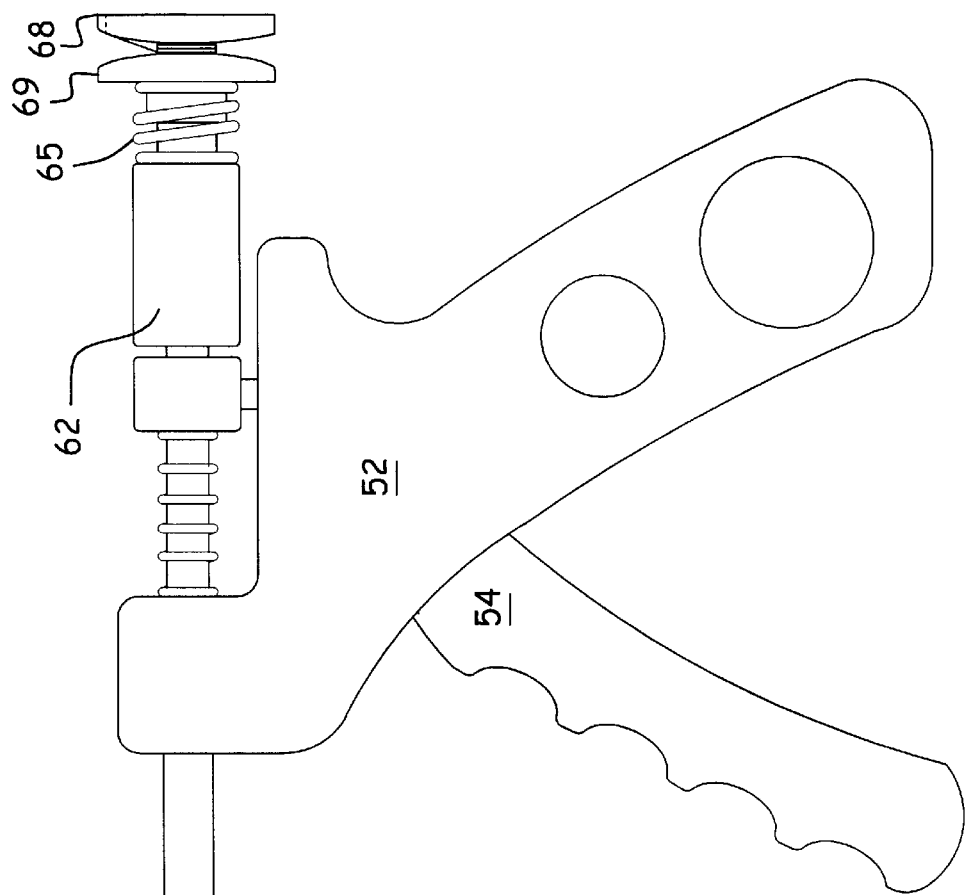
FIG. 11 is a side view of the instrument of FIG. 1 with a distal end placed adjacent a hole formed through bone tissue.
Figure 12:
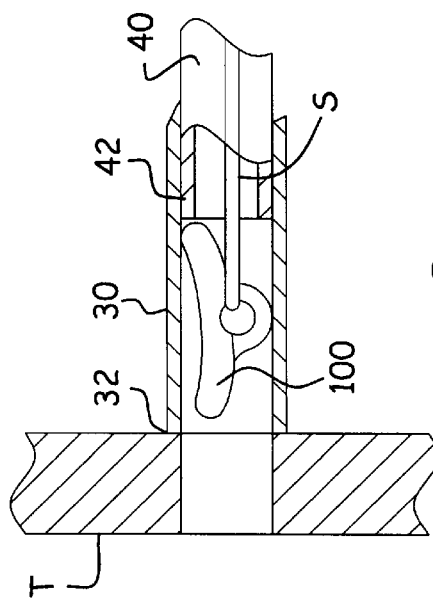
FIG. 12 is a sectional view of the distal end of the instrument in the position of FIG. 11.

From the position illustrated in FIG. 8, suture anchor 100 can be pivoted manually to a longitudinal orientation in which the longitudinal axis of suture anchor 100 corresponds substantially with the longitudinal axis of guide 30 and pusher 40, and pivotal handle 54 can be released partially, as illustrated in FIGS. 9 and 10. Note that width W of arcuate body 102 is large enough to prevent suture anchor 100 from entering distal end 42 of pusher 40 to thereby maintain the tension on suture material S regardless of the orientation of suture anchor 100. Also, when suture anchor 100 is moved to the longitudinal orientation, eyelet 108 is moved distally to place additional tension on suture material S and further compress coil spring 63. With suture anchor 100 in the longitudinal orientation, pivotal handle 54 is released completely and thus moves away from fixed handle 52 due to the force of spring 58, and therefore, distal end 42 of pusher 40 and suture anchor 100 are drawn into distal end 32 of guide 30, as illustrated in FIGS. 11 and 12. Note that the relative dimensions of suture anchor 100 and the inner diameter of guide 30 are adjusted to maintain the substantially longitudinal orientation of suture anchor 100 when suture anchor 100 is disposed inside guide 30.

The position illustrated in FIGS. 11 and 12 is referred to herein as the "loaded" position or state, i.e. suture anchor 100 is loaded in instrument 20. FIG. 11 illustrates the instrument in a loaded state with distal end 32 of guide 30 pressed against tissue T around a hole formed in tissue T, such as bone tissue. Note that distal end 32 can be introduced to the area proximate the bone through a portal sleeve disposed in a puncture created by an obturator, such as a trocar, or through other minimally invasive procedures. Also, distal end 32 can be introduced through an incision in open surgery.

Figure 13:
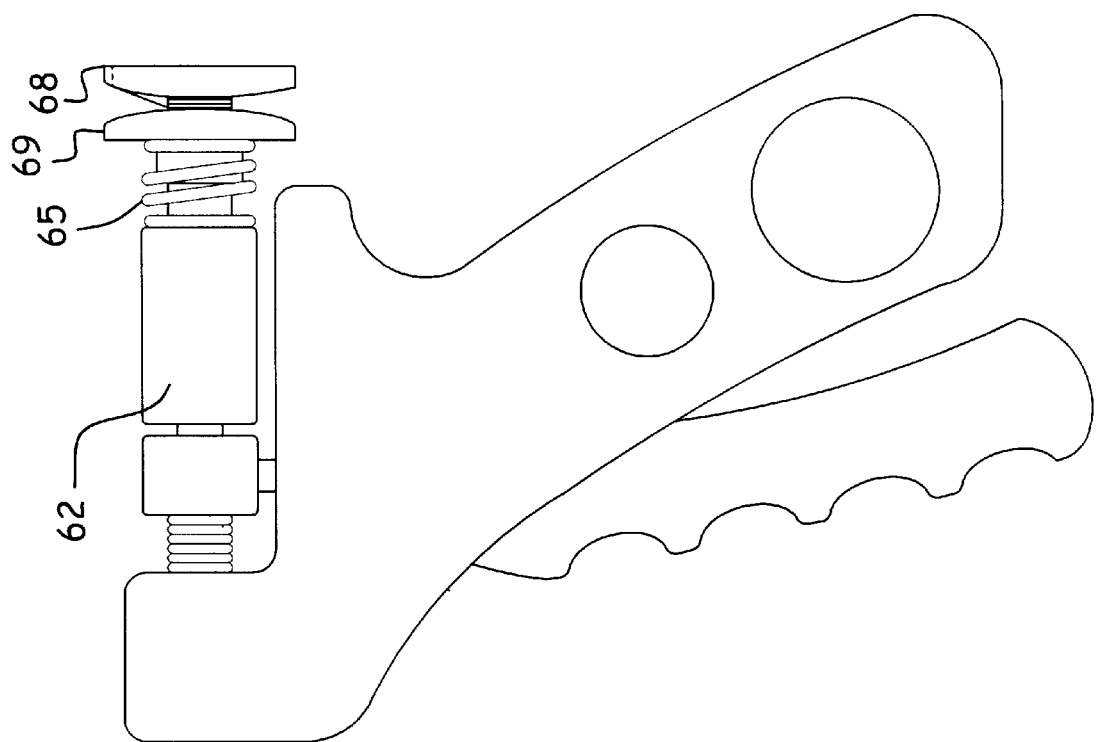
FIG. 13 is a side view of the instrument of FIG. 1 after an anchor has been inserted through a hole in bone tissue.

From the position illustrated in FIG. 11, pivotal handle 54 is pressed toward fixed handle 52 to cause pusher 40 to move distally. Since suture tensioning mechanism 60 is coupled to pusher 40, the tension on suture material S remains constant during movement of pusher 40. When pusher 40 advances far enough to move suture anchor 100 out of guide 30 and through the hole formed in tissue T, suture anchor 100 will no longer be constrained in the longitudinal orientation. Accordingly, as illustrated in FIGS. 13 and 14, suture anchor 100 will rotate to a position in which the longitudinal axis of suture anchor 100 is transverse to the longitudinal axis of guide 40, i.e the "transverse orientation".

Figure 14:
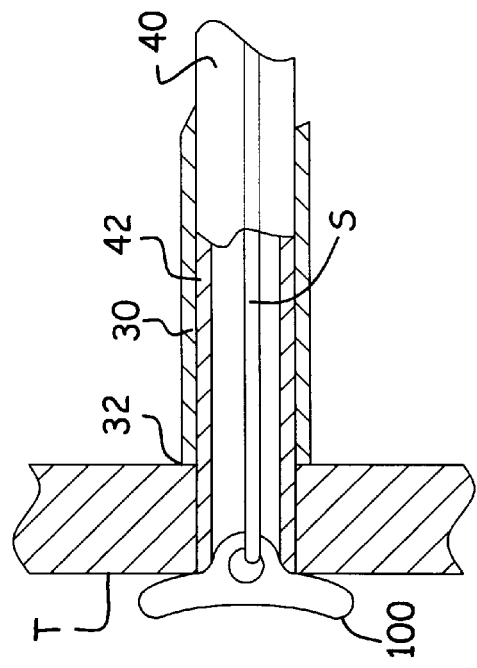
FIG. 14 is a sectional view of the distal end of the instrument in the position of FIG. 13.

Note that the diameter of the hole formed in tissue T is set to substantially correspond to the inner diameter of guide 30 thus permitting distal end 32 of guide 30 to abut tissue T and permitting distal end 42 of pusher 40 to pass through the bore, as best illustrated in FIG. 14. With suture anchor 100 in the transverse orientation, suture anchor 100 bridges the hole formed in tissue T, abuts an outer or inside surface of tissue T, and cannot pass back through the hole formed in tissue T. In this manner suture material S is fixed to tissue T and soft tissue or the like can be attached to the suture material in a known manner. To remove instrument 20 suture material S is unwrapped from around tube 67 and instrument 20 is withdrawn, as illustrated in FIGS. 15 and 16, while free ends of suture material S are manually grasped.

Various elements, such as soft tissue, can be attached to suture material S in a known manner. The hole is formed in tissue T through known minimally invasive or open procedures. The relative dimensions of the pusher, guide, suture anchor, and hole are predetermined to facilitate insertion of the suture anchor in the longitudinal orientation and subsequent movement to the transverse orientation. The convex surface of the suture anchor facilitates seating of the suture anchor in the hole. However, the suture anchor may have any shape that permits insertion through the hole and subsequent bridging of the hole. For example, the suture anchor can be rectangular, cylindrical, or triangular. Also, the suture anchor can be flexible or made of one or more pivoting parts to expand after being inserted through the hole to prevent the suture anchor from passing back through the hole.

The preferred embodiment is used with a suture anchor for attaching suture to tissue. However, the instrument can be used with any type of operating member having suture material attached thereto and the instrument can be used in various procedures. For example, the invention can be applied to a ligating procedure or any procedure in which it is desirable to maintain tension on suture while manipulating an operating member coupled to the suture. The means for manipulating the operating member can be of any form to manipulate the operating member in any desired manner.

The cross sectional shape of the guide and pusher can be varied. For example, the cross-sectional shape of either or both of the guide and pusher can be square, rectangular, triangular or any appropriate shape. The operating member can be retained in position by the general shape of the guide or by inserts placed inside the distal end of the guide. The suture can be fixedly or releasably attached to the operating member.

The disclosed mechanisms for causing relative movement between the guide and the pusher, for retaining the free ends of the suture material, and for placing tension on the suture material are only exemplary and any structure can be used to accomplish these functions.

Inasmuch as the present invention is subject to many variations, modifications and changes in detail, it is intended that all subject matter discussed above or shown in the accompanying drawings be interpreted as illustrative only and not be taken in a limiting sense.

What is claimed:

1. An instrument for manipulating an operating member during a surgical procedure, said operating member having suture material attached thereto, said instrument comprising:

a shaft having distal and proximal ends;

means for manipulating the operating member disposed at said distal end of said shaft;

a handle mechanism coupled to said means for manipulating; and a suture tension mechanism configured to retain tension on the suture material attached to the operating member when the operating member is manipulated by said means for manipulating;

said suture tension mechanism comprising a projection formed on an outer surface of said proximal end of said shaft, a barrel having first and second end faces having first and second openings formed therein, respectively, said barrel being slidingly disposed on said proximal end of said shaft with a portion of said proximal end of said shaft being received in said first opening, said projection being disposed inside said barrel between said first and second end faces, a first suture material retaining member comprising a tube extending from said second end face and a first flange fixedly disposed on said tube, a second suture material retaining member comprising a second flange slidably disposed on said tube, first biasing means for biasing said second flange toward said first flange, and second biasing means for biasing said barrel proximally with respect to said shaft;

said first biasing means comprising a first biasing member disposed between an outer surface of said second end face and said second flange.

2. An instrument for manipulating an operating member during a surgical procedure, said operating member having suture material attached thereto, said instrument comprising:

a shaft having distal and proximal ends;

means for manipulating the operating member disposed at said distal end of said shaft;

a handle mechanism coupled to said means for manipulating; and a suture tension mechanism configured to retain tension on the suture material attached to the operating member when the operating member is manipulated by said means for manipulating;

said suture tension mechanism comprising a projection formed on an outer surface of said proximal end of said shaft, a barrel having first and second end faces having first and second openings formed therein, respectively, said barrel being slidingly disposed on said proximal end of said shaft with a portion of said proximal end of said shaft being received in said first opening, said projection being disposed inside said barrel between said first and second end faces, a first suture material retaining member comprising a tube extending from said second end face and a first flange fixedly disposed on said tube, a second suture material retaining member comprising a second flange slidably disposed on said tube, first biasing means for biasing said second flange toward said first flange, and second biasing means for biasing said barrel proximally with respect to said shaft;

said second biasing means comprising a second biasing member disposed between said projection and an inner surface of said second end face.

3. A suture anchor insertion instrument for inserting an anchor having suture material attached thereto through a hole formed in tissue and orienting the anchor to span the hole with the suture material extending through the hole to facilitate attaching various members to the tissue, said instrument comprising:

a tubular guide having a proximal end and a distal end that is configured to receive the anchor in a first orientation;

a tubular pusher extending substantially through said guide and having a proximal end and a distal end that is configured to abut the anchor received in said distal end of said guide, said proximal end of said pusher extending proximally beyond said proximal end of said guide;

a handle mechanism coupled to said proximal end of said guide and said proximal end of said pusher and being operative to cause relative movement between said guide and said pusher to thereby push the anchor out of said distal end of said guide; and a suture tension mechanism configured to retain tension on the suture material attached to the anchor when the anchor is received in said distal end of said guide and pushed out of said distal end of said guide by said pusher;

said suture tension mechanism comprising a projection formed on an outer surface of said proximal end of said pusher, a barrel having first and second end faces having first and second openings formed therein, respectively said barrel being slidingly disposed on said proximal end of said pusher with a portion of said proximal end of said pusher being received in said first opening, said projection being disposed inside said barrel between said first and second end faces, a first suture material retaining member comprising a tube extending from said second end face and a first flange fixedly disposed on said tube, a second suture material retaining member comprising a second flange slidably disposed on said tube, first biasing means for biasing said second flange toward said first flange; and second biasing means for biasing said barrel proximally with respect to said pusher;

said first biasing means comprising a first biasing member disposed between an outer surface of said second end face and said second flange.

4. A suture anchor insertion instrument for inserting an anchor having suture material attached thereto through a hole formed in tissue and orienting the anchor to span the hole with the suture material extending through the hole to facilitate attaching various members to the tissue, said instrument comprising:

a tubular guide having a proximal end and a distal end that is configured to receive the anchor in a first orientation;

a tubular pusher extending substantially through said guide and having a proximal end and a distal end that is configured to abut the anchor received in said distal end of said guide, said proximal end of said pusher extending proximally beyond said proximal end of said guide;

a handle mechanism coupled to said proximal end of said guide and said proximal end of said pusher and being operative to cause relative movement between said guide and said pusher to thereby push the anchor out of said distal end of said guide; and a suture tension mechanism configured to retain tension on the suture material attached to the anchor when the anchor is received in said distal end of said guide and pushed out of said distal end of said guide by said pusher;

said suture tension mechanism comprising a projection formed on an outer surface of said proximal end of said pusher, a barrel having first and second end faces having first and second openings formed therein, respectively, said barrel being slidingly disposed on said proximal end of said pusher with a portion of said proximal end of said pusher being received in said first opening, said projection being disposed inside said barrel between said first and second end faces, a first suture material retaining member comprising a tube extending from said second end face and a first flange fixedly disposed on said tube, a second suture material retaining member comprising a second flange slidably disposed on said tube, first biasing means for biasing said second flange toward said first flange; and second biasing means for biasing said barrel proximally with respect to said pusher;

said second biasing means comprising a second biasing member disposed between said projection and an inner surface of said second end face.

* * * * *